United States Patent
Cannon et al.

(10) Patent No.: US 11,830,593 B2
(45) Date of Patent: *Nov. 28, 2023

(54) RESOLVING AMBIGUOUS SEARCH QUERIES

(71) Applicant: Cerner Innovation, Inc., North Kansas City, MO (US)

(72) Inventors: Paul Cannon, Kansas City, MO (US); Charles Donnici, Liberty, MO (US); Tanner Marvin, Lee's Summit, MO (US); Joshua Brasel, Kansas City, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/970,785

(22) Filed: Oct. 21, 2022

(65) Prior Publication Data

US 2023/0044159 A1 Feb. 9, 2023

Related U.S. Application Data

(63) Continuation of application No. 16/513,155, filed on Jul. 16, 2019, now Pat. No. 11,568,968, which is a
(Continued)

(51) Int. Cl.
*G16H 10/60* (2018.01)
*G06F 16/951* (2019.01)
(Continued)

(52) U.S. Cl.
CPC ....... *G16H 10/60* (2018.01); *G06F 16/24568* (2019.01); *G06F 16/951* (2019.01); *G16Z 99/00* (2019.02)

(58) Field of Classification Search
CPC .................................................... G16H 10/60
See application file for complete search history.

(56) References Cited

U.S. PATENT DOCUMENTS 8,805,900 B2 8/2014 Curran et al.
2005/0222976 A1* 10/2005 Pfleger .................. G06F 16/951
(Continued)

OTHER PUBLICATIONS

Final Office Action dated Oct. 3, 2016 in U.S. Appl. No. 14/266,352, 11 pages.
(Continued)

*Primary Examiner* — Evangeline Barr
(74) *Attorney, Agent, or Firm* — Invoke (57) ABSTRACT

Computerized systems and methods facilitate searches by identifying instances in which search input is an ambiguous query and resolving the ambiguous query. The search system identifies ambiguous queries by querying a common data store prior to querying a patient database. More particularly, when the search system receives search input entered into a search tool, the search system queries the common name data store before querying the patient database to determine if the search input matches a common name and is an ambiguous query. If so, the search system may provide a notification to the user to indicate the search input is an ambiguous query with a common name and prompt the user to enter additional search criteria. In some instances, the search system may prevent a search from being performed on the patient database if the search input matches a common name until additional search criteria is entered.

22 Claims, 7 Drawing Sheets

Related U.S. Application Data continuation of application No. 14/266,362, filed on Apr. 30, 2014, now abandoned.

(51) Int. Cl.
*G06F 16/2455* (2019.01)
*G16Z 99/00* (2019.01)

(56) References Cited

U.S. PATENT DOCUMENTS

| | | |
|---|---|---|
| 2006/0248078 A1 | 11/2006 | Gross et al. |
| 2006/0294092 A1 | 12/2006 | Giang et al. |
| 2009/0077071 A1* | 3/2009 | Mishkanian ......... G06F 16/951 707/999.005 |
| 2010/0169341 A1 | 7/2010 | Hu et al. |
| 2010/0180199 A1* | 7/2010 | Wu ..................... G06F 40/295 715/256 |
| 2011/0087686 A1 | 4/2011 | Brewer et al. |
| 2012/0317097 A1 | 12/2012 | Tseng |
| 2013/0103422 A1 | 4/2013 | Skocic |
| 2014/0101191 A1* | 4/2014 | Aleksovski ......... G06F 16/3322 707/767 |
| 2014/0280115 A1 | 9/2014 | Collin |
| 2015/0120689 A1* | 4/2015 | Miao ..................... G06F 16/951 707/706 |
| 2015/0317311 A1 | 11/2015 | Cannon et al. |
| 2015/0317393 A1 | 11/2015 | Cannon et al. |

OTHER PUBLICATIONS

Final Office Action received for U.S. Appl. No. 14/266,362, dated Feb. 24, 2017, 17 pages.
First Action Interview Office Action received for U.S. Appl. No. 14/266,362, dated Oct. 26, 2016, 6 pages.
Non-Final Office Action dated May 3, 2016 in U.S. Appl. No. 14/266,352, 15 pages.
Preinterview First Office Action received for U.S. Appl. No. 14/266,362, dated Aug. 12, 2016, 5 pages.

* cited by examiner

PATIENT SEARCH

⚠ × YOUR CURRENT SEARCH FILTERS HAVE COMMON NAMES. THIS WILL FAIL TO RETURN RESULTS. ADD ADDITIONAL SEARCH FILTERS. — 802

LAST NAME:

FIRST NAME:

ENCOUNTER IDENTIFIER:

PERSON IDENTIFIER:

BIRTH DATE: //****

PHONE NUMBER:

SEARCH    RESET

NO PERSONS FOUND.

NO ENCOUNTERS FOUND.

SEARCH QUALITY
☐ ASSUME WILDCARDS

OK    CANCEL    PREVIEW 800
804 (SEARCH)

FIG. 9.

RESOLVING AMBIGUOUS SEARCH QUERIES

CROSS-REFERENCE TO RELATED APPLICATIONS

This application is a continuation of U.S. application Ser. No. 16/513,155, filed on Jul. 16, 2019, which is a continuation of U.S. application Ser. No. 14/266,362, filed on Apr. 30, 2014. This application is also related by subject matter to the invention disclosed in U.S. application Ser. No. 14/266,352, filed on Apr. 30, 2014. Each of the aforementioned is hereby incorporated in this application by reference.

BACKGROUND

Managing patient records in a clinical computing environment has proven to be a challenging task. A health care system may have a number of facilities that each receives a large number of patients over a period of time, resulting in a significant number of patient records for the health care system. Given the number of patient records, it may be difficult for a user in the health care system to find the records for a particular patient. Often, clinical computing environments provide a patient search tool that allows users to enter search input to search for a particular patient. These search tools are generally successful when the search input is unique to a particular patient, such as when the search input is a social security number, medical record number assigned to a patient by the health care system, or a phone number. However, in some cases, the search input may be ambiguous, which may result in a large number of search results being returned or causing the search to take an amount of time that is unacceptable to the user performing the search. This may be the case when users perform a patient search using only a patient's name. If too many search results are returned, the user may inadvertently select the wrong patient record. Alternatively, the user may not find the desired patient and create a new patient record, which may result in multiple patient records for a single patient.

BRIEF SUMMARY

Embodiments of the present invention generally relate to techniques to improve searches on patient databases by resolving ambiguous search queries. In some embodiments, ambiguous search queries are identified by querying a common name data store prior to querying a patient database. The common name data store stores information regarding common names, including common first names, last names, and/or combinations of first and last names. When a search system receives search input, the search system queries the common name data store prior to querying the patient database to determine if the search input matches a common name and is an ambiguous query. If so, the search system may provide a notification to the user to indicate the search input is an ambiguous query with a common name and prompt the user to enter additional search criteria. In some cases, the search system may prevent a search from being performed on the patient database using the search input until additional search criteria is entered.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention are generally directed to computerized methods and systems that provide improvements to patient searches. In accordance with some embodiments of the present invention, a common name data store is provided that lists common names appearing in a patient database. The common names may include, for instance, common first names, common last names, and/or common combinations of first and last names. The common names data store may be generated by querying the patient database to identify names that occur in the patient database more frequently than some configurable threshold number.

After the common names database is generated, it may be periodically updated or regenerated to account for changes in the patient database.

The common names data store may be employed when users enter search input into a patient search tool to identify instances in which users have entered a common name that may result in a large number of search results or a search that takes an unacceptable amount of time to process. When a user enters search input, the common names data store is queried to determine if the search input matches a common name in the common names data store. If a match is determined, a notification may be provided to the user that indicates that the user input corresponds with a common name and/or that additional search input should be provided. In some embodiments, the notification may be provided if the user input is limited to the common name. If additional search input is received that may serve to narrow the search, the notification may not be provided. In some embodiments, the presence of a common name may also prevent a search from being performed on the patient database.

In accordance with further embodiments, another mechanism to improve patient searches is a search quality indicator that is provided to give a user an indication of the quality of a patient search based on the search input provided by the user. The search quality indicator may be presented to the user as the user enters the search input but before querying the patient database. This allows the user to view the search quality indicator and determine whether additional search input should be provided. When a user enters search input into a search tool, a search quality score is calculated before querying the patient database. The search quality score may be generated as a function of the amount of search input provided and/or the type of search criteria provided. In some embodiments, an algorithm may be employed that estimates the likelihood of getting a search result set using the search input that will allow the user to identify a search result corresponding with a desired patient. The algorithm may apply weightings to different types of search criteria (e.g., last name, first name, encounter identifier, person identifier, birth date, phone number, etc.) based on the perceived ability of each type of search criteria to identify a desired patient. In some embodiments, the search quality score may be based at least in part on determining if the search input includes a name that matches a common name in the common name data store. A search quality indicator is presented to the user based on the search quality score. By viewing the search quality indicator, the user may determine whether to provide additional search input before having the patient search performed.

Figure 1:
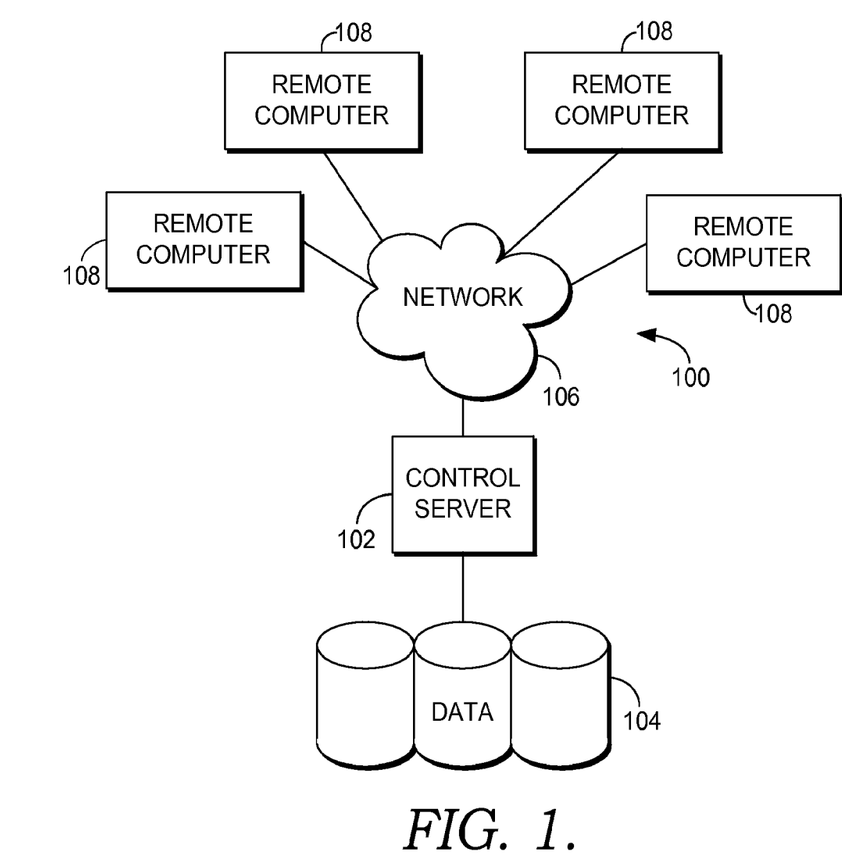
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
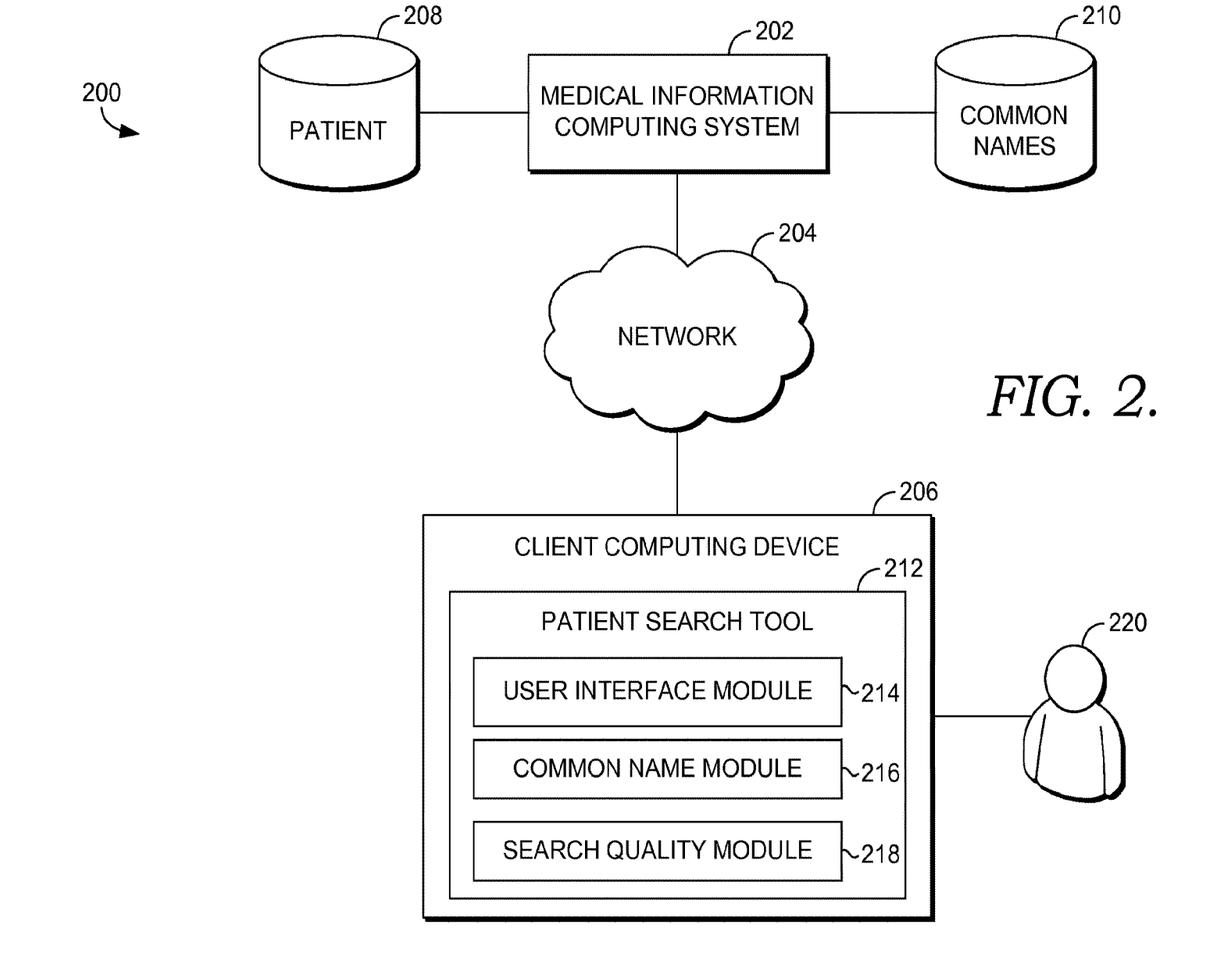
FIG. 2 is a block diagram of an exemplary system architecture in which embodiments of the invention may be employed.

Referring now to FIG. 2, a block diagram is provided illustrating an exemplary system 200 in which a patient search tool 212 is provided that allows a user 220 to search for patients in a patient database 208. In the embodiment shown in FIG. 2, the patient database 208 is provided by a medical information computing system 202, which may be a comprehensive computing system within a clinical environment similar to the exemplary computing system 100 discussed above with reference to FIG. 1. In other embodiments, the patient database 208 may be provided separate from any comprehensive clinical computing system.

The patient search tool 212 is shown in FIG. 2 as residing on a client computing device 206 which communicates with the medical information computing system 202 and patient database 208 over a network 204. However, it should be understood that the patient search tool 212 may be located at any of a variety of different locations, including, for instance, as part of the medical information computing system 202, as a stand-alone component, or distributed across multiple devices. Any and all such variations are contemplated to be within the scope of embodiments of the present invention.

Among other things, the patient search tool 212 includes a user interface module 214, a common name module 216 and a search quality module 218. The user interface module 214 generally operates to provide a patient search user interface (UI). The patient search UI allows a user to enter search input and to initiate a patient search on the patient database 208 using the entered search input.

Figure 3:
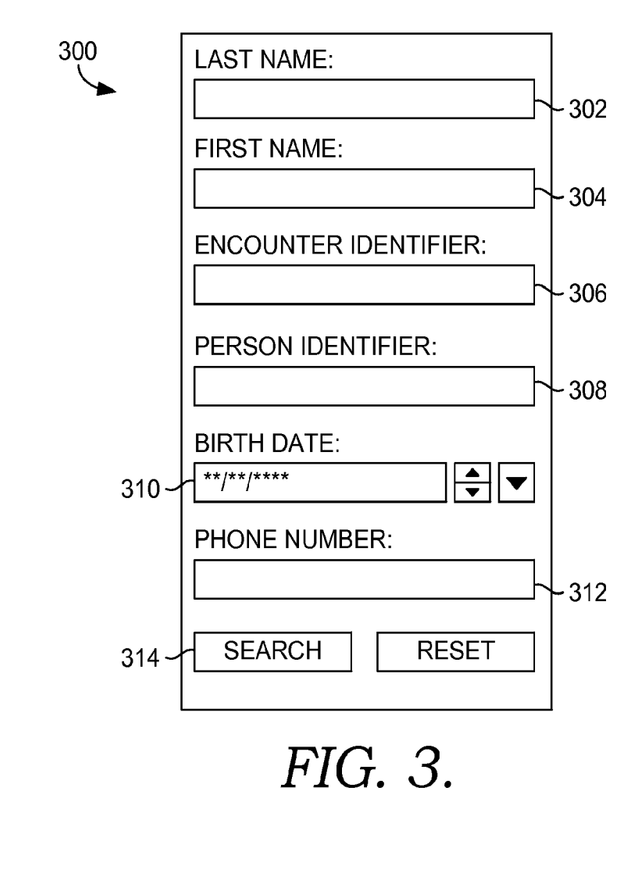
FIG. 3 is a screenshot of an exemplary patient search user interface with multiple search input fields.

In some embodiments, the patient search UI may include a single input field for a user to enter search input. In other embodiments, the patient search UI may include a number of different input fields that each correspond with a different type of search criteria. By way of example only and not limitation, FIG. 3 illustrates a patient search UI 300 that includes several input fields. The input fields include a last name input field 302, a first name input field 304, an encounter identifier input field 306, a person identifier input field 308, a birth date input field 310, and a phone number input field 312. As used herein, an "encounter identifier" is a unique identifier used to identify not only a particular patient but also a particular transaction for the patient at the health care provider. For instance, the encounter identifier may be a financial number. As used herein, a "person identifier" is an identifier that uniquely identifies a patient. For instance, the person identifier may be a social security number or a medical record number (MRN), which is a unique record number a health care provider assigns to a patient.

Referring again to FIG. 2, the common name module 216 is configured to identify searches that are directed to common names in order to notify the user and/or prevent a search from being performed that will return too many results due to the common name. To facilitate the identification of common names, the system 200 includes a common names data store 210. The common names data store 210 lists common names appearing in the patient database 208. This may include first names, last names, and/or combinations of first names and last names. In some embodiments, the common names may be identified by analyzing the patient database 208 to identify any names (first, last, and/or combinations) that appear in the patient database 208 more than some configurable number (e.g., more than 200 times).

Although the common names data store 210 is shown as part of the medical information computing system 202, the common names data store 210 may be provided separate from any comprehensive clinical computing system. Additionally, although the common names data store 210 is shown separate from the patient database 208, in some embodiments, the common names data store 210 may be stored in conjunction with the patient database 208, although the patent database 208 and common names data store 210 are separately searchable.

By employing a common names data store 210 when patient searches are being performed, the common name module 216 may quickly identify common names without having to search the entire patient database 208, which may be a time consuming process. When a user enters search input into the patient search UI provided by the user interface module 214, the common name module 216 queries the common names data store 210 to determine whether the search input matches a common name.

In some embodiments, the common name module 216 may automatically query the common names data store 210 while the user is entering the search input before the user provides any command to initiate a patient search (e.g., by selecting a search button, such as the search button 314 shown in FIG. 3). The common names data store 210 may be automatically queried each time the user types a new character into the patient search UI or on some other basis (e.g., every second) as the user enters search input. In other embodiments, the common name module 216 may query the common names data store 210 after the user provides some explicit command to perform a patient search (e.g. by selecting the search button 314 shown in FIG. 3).

When the common name module 216 determines the user input matches a common name in the common names data store 210, a notice may be provided for presentation to the user. The notice may provide information such as an indication that the search input includes a common name, the search will return too many results, and/or additional search criteria should be entered. In some embodiments, a match is determined if the user input is an exact match (as opposed to a partial match) for a name in the common name data store 210. Additionally, in some embodiments, the notice may be provided only if the search input is limited to a name matching the common name. In such embodiments, if additional search input is provided (e.g., encounter identifier, person identifier, birth date, phone number, first or last name that creates a non-common combination when a common first or last name is provided, etc.), the notice may not be provided as the additional search input may serve to properly narrow the search.

In some embodiments, if it is determined the user input matches a common name, the search tool 212 may not allow a search to be performed on the patient database 208. For instance, the search button 314 in FIG. 3 may not be selectable by the user to initiate a search if a common name is identified (and additional search criteria is not provided in accordance with some embodiments). In other embodiments, if a common name match is determined, a search may still be performed, but the results may be limited to a particular number (e.g., 200 results).

The search quality module 218 is generally configured to provide a search quality indicator based on the search input provided by a user. The search quality indicator provides an indication of the quality of the search in the sense of a likelihood of getting a set of one or more search results that allows the user to find a desired patient. Ideally, a search would provide a search result corresponding only with the desired patient. A small set of search results that include the desired patient also allows a user to quickly find the patient. However, an ambiguous query may result in a large set of search results that makes it hard to find the desired patient or may not even include the desired patient if the search results provided to the user are limited to a maximum number of results. Additionally, an ambiguous query may result in a search that takes an unacceptable amount of time to process.

The search quality module 218 may employ an algorithm to determine a search quality score based on the user's search input received by the patient search UI provided by the user interface module 214. The algorithm generates a search quality score that provides an indication of search quality without querying the patient database 208. Instead of querying the patient database 208, the algorithm may operate on the search input received by the patient search UI.

In accordance with some embodiments of the present invention, the algorithm employed by the search quality module 218 may assign different weightings to different types of search criteria based on the perceived ability of the different types of search criteria to limit the search to a smaller set of search results likely to include a desired patient. By way of example only and not limitation, a person identifier or encounter identifier may correspond with a single patient and therefore these types of search criteria may receive higher weighting. A phone number may also correspond with a single patient and therefore receive higher weighting. A birth date may correspond with multiple patients, although the number of patients may not be a large number, and therefore birth date search criteria may receive medium weighting. A last name may be shared by many patients and may therefore receive lower weighting. A first name may be shared by even more patients and may therefore receive even lower weighting.

As can be understood, the weightings only provide an approximation of search quality (e.g., the number of search results likely to be returned). For instance, a particular patient may have a unique first name but the patient may share a birthdate with multiple patients. In that example, the patient's first name actually serves as better search criteria than the birthdate. However, the algorithm and weightings don't take actual patient records into consideration but merely serve as a general rule approximation.

In the instances in which the patient search UI provides input fields corresponding with different search criteria (e.g., the patient search UI 300 of FIG. 3), the search quality module 218 may determine which input field(s) has/have received input and apply weightings based on the type of search criteria corresponding with those input field(s). In some embodiments, multipliers may be provided if search input has been provided in a combination of input fields. Additionally, the algorithm may generate the score based on the amount of text being provided in an input field. For instance, the more text received in an input field, the higher the score.

If a single search input field is provided by the patient search UI, the algorithm may generate a score based on the amount of text provided in the input field. For instance, more text entered into the input field may cause the search quality score to increase. The algorithm may also attempt to determine the type of search criteria provided in the single input field. For instance, the input text may be analyzed to determine if the input likely corresponds with a first name, last name, encounter identifier, person identifier, birth date, phone number, etc. This may be based on the presence of letters versus numbers, the number of characters entered, and other considerations. If the type of search criteria is determined, a weighting may be applied based on the type of search criteria as discussed above.

In some embodiments, the algorithm employed by the search quality module 218 may consider common names from the common names data store 210 when generating a search quality score. In particular, if a first name, last name, or combination of first and last name is received as search input, the common names data store 218 may be queried to determine if the input corresponds with a common name. If so, the search quality score may be lowered based on the presence of a common name. In some instances, if the search input corresponds with a common name and additional input has not been received for other search criteria, a minimum search quality score may be provided.

Figure 4:
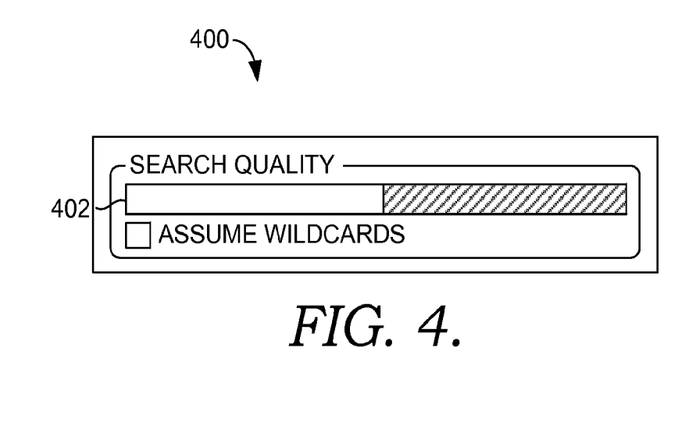
FIG. 4 is a screenshot of an exemplary search quality indicator in accordance with an embodiment of the present invention.

A search quality indicator based on the search quality score is presented to the user. By providing the search quality indicator, the user may quickly determine whether the user has provided sufficient search input or if additional input should be provided to narrow the search. The search quality indicator may be a numerical score or some graphical indicator, such as a color that represents search quality and/or a bar whose length corresponds with search quality. By way of example only and not limitation, FIG. 4 illustrates an example search quality indicator 400 that may be presented to the user. The length of the bar 402 provides an indication of the search quality with a longer bar 402 indicating a higher search quality.

The search quality indicator may be updated as the user enters search input into a patient search UI. For instance, the search quality score and search quality indicator may be updated each time the user enters additional text (e.g., as each character is typed) or deletes text. The search quality score and search quality indicator could be updated based on some other basis, such as a time basis. For instance, they could be updated every second.

In some embodiments, if the search quality score is below some threshold score, the search tool 212 may not allow a search to be performed on the patient database 208 using the search input. For instance, the search button 314 in FIG. 3 may not be selectable by the user to initiate a search if the search quality score is below the threshold score. In other embodiments, if the search quality score is below the threshold score, a search may still be performed, but the results may be limited to a particular number (e.g., 200 results). A notification may be presented to the user indicating that a search cannot be performed or the number of search results is limited because the search quality score is too low.

Figure 5:
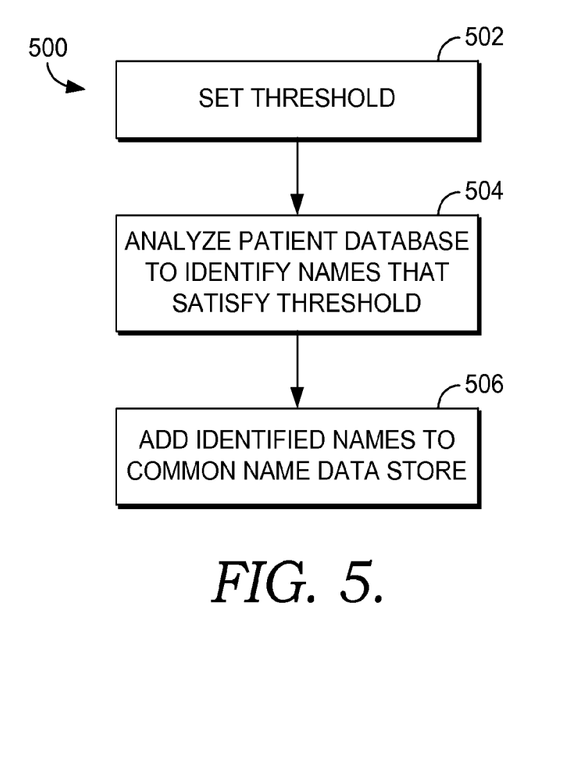
FIG. 5 is a flow diagram showing a method for generating a common name data store in accordance with an embodiment of the present invention.

Turning to FIG. 5, a flow diagram is provided that illustrates a method 500 for generating a common name data store in accordance with an embodiment of the present invention. As shown at block 502, a threshold is established for common names. The threshold may simply be a number of times a name appears within the patient database that will trigger the name being considered a common name. For example, the threshold could be a name appearing in the patient database 200 times. The threshold may be configurable, for instance, based on the size of the domain and other parameters that impact the performance of the patient name search function.

The patient database is analyzed at block 504 to identify names that satisfy the threshold. In particular, any first name, any last name, and any combination of first and last names that appears within the patient database a certain number of times that satisfies the threshold is identified as a common name. For example, if the threshold is set at 200, first names, last names, and combinations of first and last names that appear within the patient database 200 or more times is identified as a common name.

The identified common names are added to a common name data store, as shown at block 506. As such, the common name data store includes common first names, common last names, and common combinations of first and last names.

Figure 6:
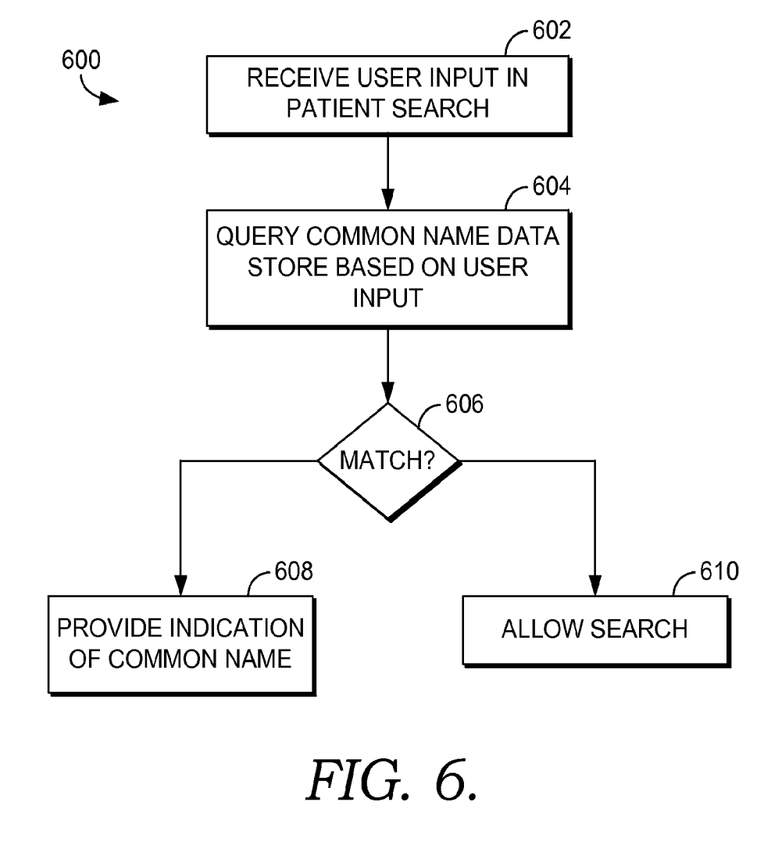
FIG. 6 is a flow diagram showing a method for employing a common name data store when a user enters patient search information in accordance with an embodiment of the present invention.

With reference now to FIG. 6, a flow diagram is provided that illustrates a method for employing a common name data store when a user enters patient search information in accordance with an embodiment of the present invention. As shown at block 602, user input is received in a patient search UI. The patient search UI may be a single search box in some embodiments. In other embodiments, the patient search UI may include a number of search input fields for various types of search criteria (e.g., last name, first name, encounter identifier, person identifier, birth date, phone number, etc.).

The common name data store is queried based on the user input, as shown at block 604. In some embodiments, the common name data store is queried after the user has selected a user interface element to initiate a search (e.g., a search button). In other embodiments, the common name data store is automatically queried as the input is entered into the patient search UI before the user has selected any button or other UI element to initiate a search. For instance, the common name data store may be automatically queried after each character is entered into the patient search UI, periodically as the query is entered (e.g., every second), or on some other basis.

Figure 7:
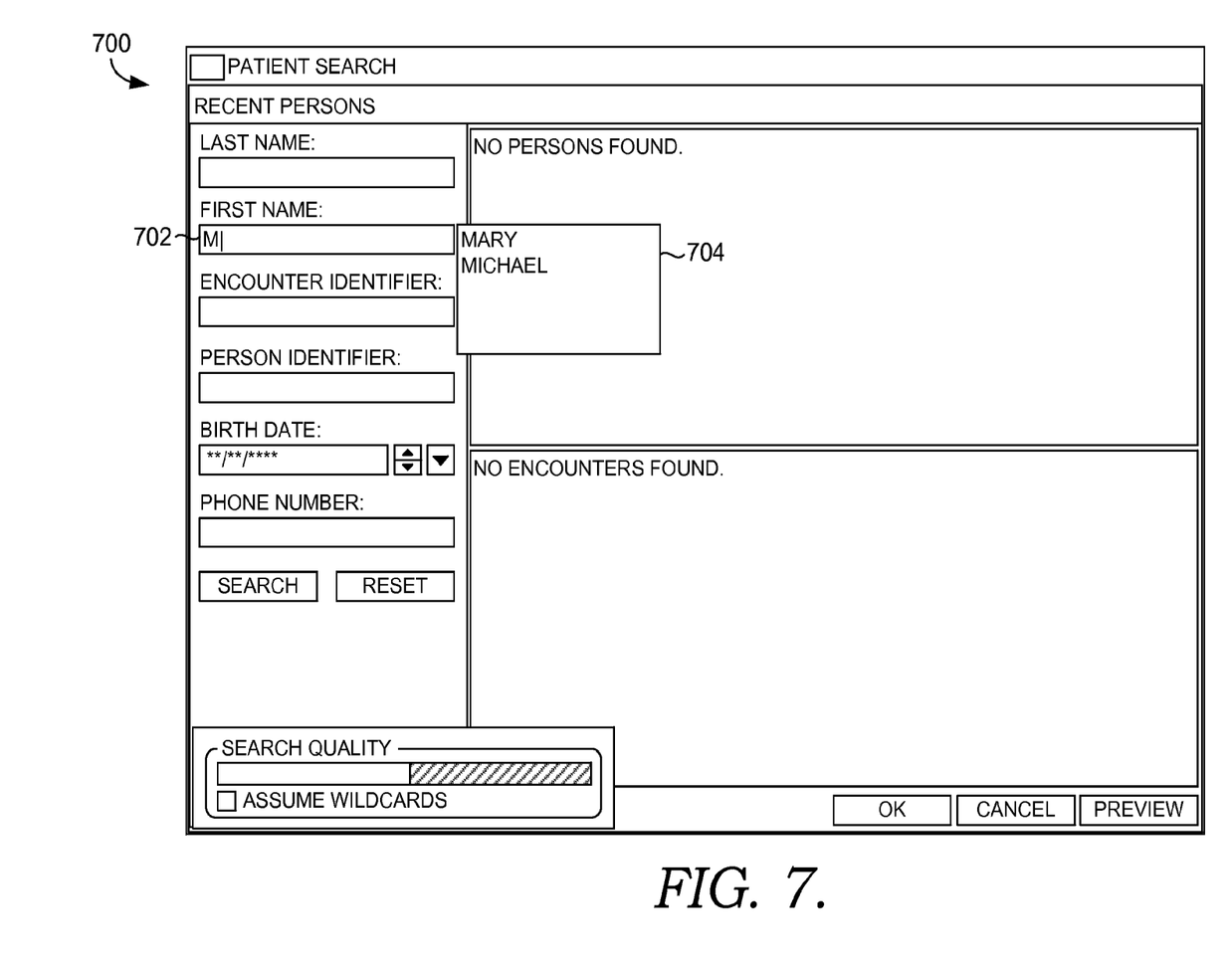
FIG. 7 is a screenshot showing an exemplary patient search user interface with a common names box indicating common names corresponding with search input in accordance with an embodiment of the present invention.

In embodiments in which the common name data store is queried as the user enters patient search information, an indication of common names that correspond with the input received at that point may be provided in the user interface. For instance, FIG. 7 shows a screenshot of a patient search UI 700 in which a user has begun to enter search information in a first name input field 702. In particular, the user has typed the letter "m." Based on this partial input, the common names "Mary" and "Michael" have been identified in the common names data store, and a box 704 is presented in the user interface 700 to show the user that these are common names matching the partial input. If the user were to continue to type, the common names included in the box 704 may be updated. For instance, if the user were to add an "a" so the search input is now "ma," only "Mary" would be presented in the box 704.

Returning to FIG. 6, as shown at block 606, a determination is made based a query to the common name data store whether the user input matches a common name in the common name data store. In some embodiments, the user input matches a common name if it is an exact match. For instance, if the user in the example of FIG. 7 were to continuing typing so the name "mary" has been entered in the first name input field 702, the system would determine the entered name exactly matches a common name in the common name data store. In other embodiments, a match may be determined if the user input is a partial match to a common name. This determination may be made automatically as the input is received without requiring the user to select a search button or the determination may be made after the user has selected the search button.

Figure 8:
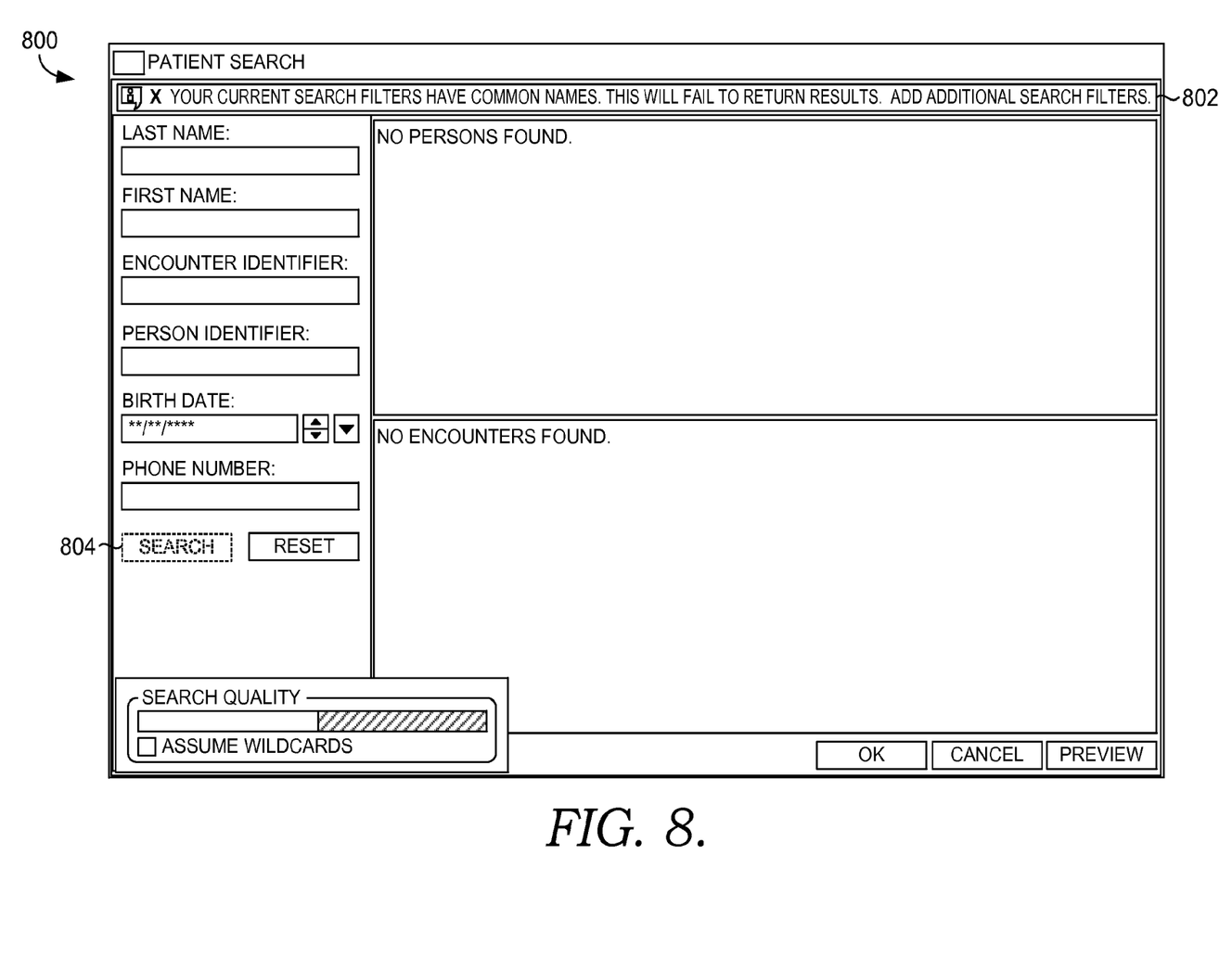
FIG. 8 is a screenshot showing an exemplary patient search user interface with a notification indicating the presence of a common name in the search criteria in accordance with an embodiment of the present invention.

If a match is determined at block 606, an indication is provided that the user has entered a common name, as shown at block 608. In some embodiments, the indication is provided if only a common name has been entered without any other search input. For instance, if additional search input, such as a telephone number or birth date, has also been entered, the indication may not be provided because the additional information may be employed to narrow the search. An example of a common name notice 802 is shown in the screenshot of FIG. 8. As shown in FIG. 8, the notice 802 may indicate that only a common name has been entered. Additionally, the notice 802 may advise the user to add additional information to narrow the search.

In some embodiments, when a common name match is determined at block 606, the system still allows a search to be performed on the patient database, but the search may return only a certain number of patient results (e.g., the first 200 patients identified from the search). In other embodiments, when a common name match is determined at block 606, the system prevents a search from being performed. For example, in instances in which the common name match is determined automatically before a search button is selected by the user, the patient search UI may be updated so that the search button cannot be selected to initiate a search. By way of example to illustrate, the search button 804 in the patient search UI 800 of FIG. 8 has been grayed out indicating that the search button 804 cannot be selected by the user. In instances in which the common name match is determined when the user selects the search button, the notice presented to the user indicating that the search is directed to a common name may also indicate that a search cannot be performed.

If it is determined at block 606 that the name entered by the user does not match a common name (and/or additional search information is included), a search may be performed on the patient database, as shown at block 610.

Figure 9:
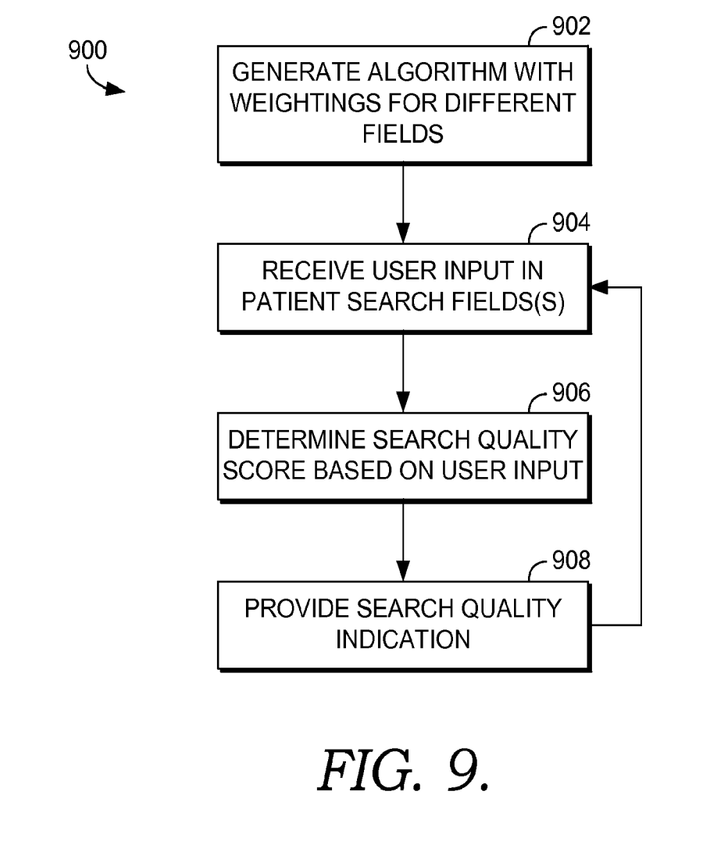
FIG. 9 is a flow diagram showing a method for providing a search quality indication in accordance with an embodiment of the present invention.

Turning now to FIG. 9, a flow diagram is provided that illustrates a method 900 for providing a search quality indication in accordance with embodiments of the present invention. As shown at block 902, an algorithm is generated for determining search quality scores based on input received in a patient search UI. As discussed previously, the algorithm may generate a search quality score that represents the likelihood of having a search result returned that allow the user to quickly find a desired patient. In some embodiments, the algorithm may apply weightings to different types of search criteria based on the perceived ability of each type of search criteria to narrow the search.

User input is received in an input field in a patient search UI, as shown at block 904. For instance, the user may type characters into an input field of the patient search UI. In some instances, the patient search UI may include a single input field, and in other instances, the patient search UI may include multiple input fields, each corresponding with a different type of search criteria.

As shown at block 906, a search quality score is determined for the user input using the algorithm generated at block 902. This may include determining the type of search criteria corresponding with the user input and applying a weighting based on that type of search criteria. Additionally, the search quality score may be based on the amount of user input received.

A search quality indication based on the search quality score is presented to the user, as shown at block 908. In some embodiments, the search quality indication presented to the user may be the search quality score or some other numerical indication based on the score. In other embodiments, a graphical representation based on the search quality score may be presented.

As shown by the return to block 904, as the user continues to enter characters in the search input fields, a new search quality score is calculated at block 906, and the search quality indication is updated at block 908. As such, the search quality indicator is continuously updated as the user continues to enter more search information. In some embodiments, the search quality indicator is updated whenever the user enters a new character or otherwise modifies the search input (e.g., deleting a character, input in a whole field, etc.). In other embodiments, the search quality indicator may be updated on a time basis (e.g., every second) or some other basis.

As can be understood, embodiments of the present invention provide techniques for improving patient searches. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory media storing computer-useable instructions that, when used by one or more computing devices, cause the one or more computing devices to initiate operations, the operations comprising:
   as a character string is received as a search input and prior to an interaction with a user interface (UI) element that is configured to submit a search query, scanning a common entry database storing a plurality of character strings for the character string, the plurality of character strings predetermined to be ambiguous based on a number of times a stored character string occurs in a patient database;
   in response to a determination that the character string corresponds to an entry in the common entry database and prior to the interaction with the UI element, displaying a visual indication via a UI that the search input includes ambiguity;
   as a modification to the character string is received, rescanning the common entry database for a modified character string, the modified character string including the character string and at least one additional character;
   responsive to a determination that the modified character string is not stored in the common entry database, removing the displayed visual indication from the UI; and
   querying the patient database using the search input based on the interaction with the UI element.

2. The one or more non-transitory media of claim 1, wherein the operations further comprise automatically querying the common entry database in response to receiving the character string.

3. One or more non-transitory media of claim 2, wherein the operations further comprise querying the common entry database in response to receiving each character inputted as part of the search input.

4. One or more non-transitory media of claim 1, wherein the character string is determined to correspond to the entry in response to the character string exactly matching the entry.

5. One or more non-transitory media of claim 1, wherein the visual indication is provided for presentation in response to no additional search input being received within a predetermined time.

6. One or more non-transitory media of claim 1, wherein the operations further comprise: in response to the determination that the character string corresponds to the entry, preventing a query from being performed on the patient database using the character string.

7. One or more non-transitory media of claim 1, wherein the operations further comprise:
determining that the character string is a partial match to one or more common names in the common entry database; and
providing an indication of the one or more common names for presentation.

8. A method, comprising:
as a character string is received as a search input and prior to an interaction with a user interface (UI) element that submits a search query, scanning a common entry database storing a plurality of character strings for the character string, the plurality of character strings predetermined to be ambiguous based on a number of times a stored character string occurs in a patient database;
in response to determining that the character string corresponds to an entry in the common entry database and prior to the interaction with the UI element, displaying a visual indication via a UI that the search input includes ambiguity;
as a modification to the character string is received, rescanning the common entry database for a modified character string, the modified character string including the character string and at least one additional character;
responsive to a determination that the modified character string is not stored in the common entry database, removing the displayed visual indication from the UI; and
querying the patient database using the search input based on the interaction with the UI element.

9. The method of claim 8, wherein the common entry database is scanned in response to receiving each character of the character string.

10. The method of claim 8, wherein the character string is determined to correspond to the entry in response to the character string exactly matching the entry.

11. The method of claim 8, wherein the visual indication is displayed after a predetermined period of time without detection of additional search input.

12. The method of claim 8, further comprising: in response to determining that the character string corresponds to the entry, preventing a query from being performed on the patient database using the character string.

13. The method of claim 8, wherein one or both of the common entry database and the patient database are included in a system, and wherein the system comprises one or more processors that perform one or more of the scanning, the displaying, the rescanning, the removing, or the querying.

14. The method of claim 8, wherein the common entry database and the patient database are included in a system, and wherein the system comprises one or more processors that perform the scanning, the displaying, the rescanning, the removing, or the querying.

15. A system, comprising:
a patient database storing information regarding a plurality of patients;
a common entry database storing a plurality of character strings, the plurality of character strings predetermined to be ambiguous based on a number of times a stored character string occurs within the patient database;
one or more processors; and
one or more computer media storing instructions that, when used by the one or more processors, cause the one or more processors to initiate operations comprising:
scanning the common entry database for a character string as the character string is received as a search input and prior to an interaction with a user interface (UI) element that is configured to submit a search query;
displaying a visual indication via a UI that the search input includes ambiguity in response to the scan identifying an entry in the common entry database corresponding to the character string;
rescanning the common entry database, for a modified character string, as a modification to the character string is received, the modification including addition of at least one character to the character string;
removing the displayed visual indication from the UI in response to the rescan of the common entry database failing to identify an entry corresponding to the modified character string; and
querying the patient database using the search input based on the interaction with the UI element.

16. The system of claim 15, wherein the operations further comprise automatically querying the common entry database after receiving the character string.

17. The system of claim 16, wherein the operations further comprise querying the common entry database in response to receiving each character entered as part of the character string.

18. The system of claim 15, wherein the character string is determined to correspond to the entry in response to the character string exactly matching the entry.

19. The system of claim 15, wherein the visual indication is displayed in response to no additional characters being received within a predetermined time.

20. The system of claim 15, wherein use of the instructions further causes the one or more processors to prevent the querying from being performed on the patient database while the character string corresponds with one of the plurality of character strings in the common entry database.

21. The system of claim 20, wherein use of the instructions further causes the one or more processors to display another visual indication indicating that submission of the query is prevented.

22. The system of claim 15, wherein use of the instructions further causes the one or more processors to determine that the character string is a partial match to at least one of the plurality of character strings in the common entry database and to provide an indication of the at least one of the plurality of character strings for presentation.

* * * * *